(12) United States Patent
Kahlert et al.

(10) Patent No.: US 11,324,658 B2
(45) Date of Patent: May 10, 2022

(54) DEVICE FOR CONTROLLING THE ENRICHMENT OF NITRIC OXIDE LEVELS AND A CONTROL METHOD

(71) Applicant: KONINKLIJKE PHILIPS N.V., Eindhoven (NL)

(72) Inventors: Joachim Kahlert, Aachen (DE); Maria Estrella Mena Benito, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 219 days.

(21) Appl. No.: 15/778,834

(22) PCT Filed: Nov. 23, 2016

(86) PCT No.: PCT/EP2016/078505
§ 371 (c)(1),
(2) Date: May 24, 2018

(87) PCT Pub. No.: WO2017/089369
PCT Pub. Date: Jun. 1, 2017

(65) Prior Publication Data
US 2018/0344566 A1    Dec. 6, 2018

(30) Foreign Application Priority Data

Nov. 27, 2015 (EP) .................................... 15196767

(51) Int. Cl.
*A61H 23/02* (2006.01)
*A61M 16/06* (2006.01)
(Continued)

(52) U.S. Cl.
CPC ..... *A61H 23/0236* (2013.01); *A61M 16/0006* (2014.02); *A61M 16/022* (2017.08);
(Continued)

(58) Field of Classification Search
CPC ................ A61H 23/0236; A61H 23/16; A61H 23/0006; A61H 23/022; A61H 23/06;
(Continued)

(56) References Cited

U.S. PATENT DOCUMENTS 5,549,655 A * 8/1996 Erickson .............. A61B 5/7221
607/42
6,308,703 B1   10/2001 Alving et al.
(Continued)

FOREIGN PATENT DOCUMENTS

WO    1997042995 A1   11/1997
WO    2003063703 A1    8/2003
(Continued)

OTHER PUBLICATIONS

Struben, V. et al., "Silent and humming nasal NO measurements in adults aged 18-70 years", European Journal of Clinical Investigation (2005) 35, pp. 653-657.
(Continued)

*Primary Examiner* — Timothy S Stanis
*Assistant Examiner* — Matthew R Moon
(74) *Attorney, Agent, or Firm* — Daniel H. Brean

(57) ABSTRACT

A device is provided for controlling the nitric oxide levels within the lungs of a subject. The device comprises a detector for detecting the respiration cycle of the subject and a stimulator for applying an acoustic or vibratory stimulus to the subject. The stimulator is controlled in dependence on the detected respiration cycle. In particular, acoustic stimulation may be provided at the onset of inspiration. In this way, the nitric oxide flow can be controlled in a way to ensure that the paranasal nitric oxide is nearly fully inspired. This provides a higher nitric oxide concentration in the lung/alveoli.

19 Claims, 1 Drawing Sheet

(51) Int. Cl.
*A61M 16/08* (2006.01)
*A61M 16/10* (2006.01)
*A61M 16/00* (2006.01)
*A61H 33/14* (2006.01)

(52) U.S. Cl.
CPC ........ *A61M 16/06* (2013.01); *A61M 16/0683* (2013.01); *A61M 16/0816* (2013.01); *A61M 16/10* (2013.01); A61H 2033/146 (2013.01); A61H 2201/107 (2013.01); A61H 2201/1604 (2013.01); A61H 2201/165 (2013.01); A61H 2201/50 (2013.01); A61H 2201/503 (2013.01); A61H 2201/5025 (2013.01); A61H 2201/5061 (2013.01); A61H 2201/5084 (2013.01); A61H 2201/5087 (2013.01); A61H 2230/50 (2013.01); A61M 2016/0036 (2013.01); A61M 2202/0275 (2013.01)

(58) Field of Classification Search
CPC ............ A61H 23/0683; A61H 23/0816; A61H 23/10; A61H 2033/146; A61H 2201/50; A61H 2201/503; A61H 2201/5061; A61H 2201/5084; A61H 2201/5087; A61H 2201/5025; A61H 2230/50; A61H 2201/107; A61H 2201/1604; A61H 2201/165; A61M 2016/0036; A61M 2202/0275
See application file for complete search history.

(56) References Cited

U.S. PATENT DOCUMENTS

| | | | |
|---|---|---|---|
| 2005/0143673 A1* | 6/2005 | Lundberg | A61B 5/082 600/532 |
| 2008/0200848 A1 | 8/2008 | Avni | |
| 2010/0275921 A1* | 11/2010 | Schindhelm | A61B 5/08 128/204.23 |
| 2011/0046432 A1* | 2/2011 | Simon | A61H 23/02 600/14 |
| 2011/0071444 A1 | 3/2011 | Kassatly | |
| 2012/0046579 A1* | 2/2012 | Radl | A61H 11/00 601/46 |
| 2015/0065904 A1 | 3/2015 | Stenzler et al. | |
| 2015/0073316 A1 | 3/2015 | Bende | |
| 2015/0290418 A1 | 10/2015 | Kaczka et al. | |
| 2020/0030567 A1 | 1/2020 | Hardin et al. | |

FOREIGN PATENT DOCUMENTS

| | | |
|---|---|---|
| WO | 2010071919 A1 | 7/2010 |
| WO | 2010113046 A1 | 10/2010 |
| WO | 2011007346 A1 | 1/2011 |
| WO | 2015168517 A1 | 11/2015 |

OTHER PUBLICATIONS

Tarhan, E. et al., "Acoustic rhinometry in humans: accuracy of nasal passage area estimates, and ability to quantify paranasal sinus volume and ostium size", J Appl Physiol 99: 616-623, 2005.

Maniscalco, M. et al., "Assessment of nasal and sinus nitric oxide output using single-breath humming exhalations", European Respiratory Journal, 2003, 22: 323-329.

Taichman, D. et al., "Inahled nitric oxide in adults with pulmonary hypertension", 2014, www.uptodate.com.

Struben, V., "Nasal nitric oxide: Methodology, normal values and potential clinical application", Nov. 2006.

Lundberg, J., "Nitric oxide and the paranasal sinuses", The Anatomical Record, 291: 1479-1484, 2008.

Serrano, C. et al., "Nasal Nitric Oside", Arch Bronconeumol, 2004: 40(5): 222-30, 2003.

* cited by examiner

US 11,324,658 B2

DEVICE FOR CONTROLLING THE ENRICHMENT OF NITRIC OXIDE LEVELS AND A CONTROL METHOD

CROSS-REFERENCE TO PRIOR APPLICATIONS

This application is the U.S. National Phase application under 35 U.S.C. § 371 of International Application Serial No. PCT/EP2016/078505, filed on 23 Nov. 2016, which claims the benefit of European Serial No. 15196767.6, filed on 27 Nov. 2015. These applications are hereby incorporated by reference herein.

FIELD OF THE INVENTION

This invention relates to the control of nitric oxide levels in the lungs of a patient.

BACKGROUND OF THE INVENTION

This invention is of interest for the treatment of pulmonary disorders.

Chronic obstructive pulmonary disease (COPD) is a progressive and highly irreversible disease that is characterized by airflow obstruction. The airflow obstruction is present because of a combination of airway and parenchymal damage. The damage is the result of chronic inflammation that differs from that seen in asthma and which is usually the result of tobacco smoke.

COPD produces symptoms, disability and impaired quality of life which may respond to pharmacological and other therapies that have limited or no impact on the airflow obstruction. Exacerbations often occur in patients with COPD, where there is a rapid and sustained worsening of symptoms beyond normal day-to-day variations. At the same time comorbidities, such as cardiovascular or psychology-related comorbidities, in patients with COPD have an important impact on disease severity and survival, as well as health status (Vanfleteren 2013).

Pulmonary hypertension, constricted and collapsed alveoli are typical symptoms in COPD patients and are a major cause of COPD exacerbation and hospital readmission. Existing medication therapy is targeted to dilate the bronchi and blood vessels in order to improve the pulmonary ventilation and circulation; however, it is critical to find an optimal dosage.

There is therefore a need for a non-drug therapy in vasodilatation and hypertension treatment both for clinical and home healthcare applications.

Nitric oxide (NO) is well known as a vasodilator, which is able to dilate but also relax blood vessels, bronchi and alveoli. The human body produces nitric oxide in the endothelial cells in the blood vessels and in the airway. The release of nitric oxide is controlled and stimulated by receptors in the wall of the blood vessels and in the airway.

In the airway, nitric oxide is in particular produced in the paranasal sinuses. The cavities of the air-filled sinuses behave as reservoirs for nitric oxide. During normal breathing due to the pressure and flow changes in the inspiration (or inhalation) and expiration (or exhalation) cycle, a part of the nitric oxide flows from the sinus into the airway. The nitric oxide is partly inspired and partly washed out and lost in the expiration phase.

The nitric oxide in the inspired air migrates in the alveoli through cell membranes into the pulmonary blood vessels and contributes to a vessel dilation and relaxation of constricted vessels, which consequently lowers the vascular resistance and the blood pressure. This has a beneficial impact on the preload and afterload of the heart and improves the cardiac stroke volume.

In the paranasal sinus, there is an equilibrium of nitric oxide production and nitric oxide flow in the airway. In case of an increased outflow the body rebalance the concentration by an increased production to achieve an equilibrium in the paranasal sinuses. The outflow of nitric oxide during expiration can be stimulated by humming, which involves voluntarily generating acoustic signals at humming frequencies.

This is for example reported in "Silent and humming nasal nitric oxide measurements in adults aged 18-70 years" of V. M. D. Struben et. al., European Journal of Clinical Investigation (2005) 35, pp. 653-657.

These humming frequencies create an acoustic resonance in the sinus and lead to an improved ventilation of the sinuses and an increased outflow of nitric oxide. This multiplies the nitric oxide concentration in the expired air by a factor of 3 to 5.

Humming frequencies created by the vocal cords during expiration leads to a strong washing out of nitric oxide from the sinus. Therefore the nitric oxide produced by the body is lost for the next inspiration event of the respiration cycle. This lowers the nitric oxide concentration in inspired air which reaches the alveoli and this is one cause of the insufficient dilatation of the blood vessels.

The flow from the sinus into the airway occurs only in nasal breathing. In oral breathing the sinuses are not ventilated and therefore the nitric oxide will be captured in the sinuses.

It is known for oral breathing (for instance in intubated patients in the intensive care unit or for persons with an insufficient nasal respiration or in COPD) that the nitric oxide concentration in the breathing air is reduced which is a cause for increased pulmonary blood pressure.

In a clinical setting in the intensive care unit, the reduced nitric oxide concentration can be compensated by a nitric oxide enhancement system from an external nitric oxide source, but this is not applicable for home healthcare solutions.

Therefore, in home applications there is a need to develop a safe and easy applicable concept for an enhancement of nitric oxide by a better use of the nitric oxide produced by the body itself without a need of external nitric oxide sources.

US 2015/290418 A1 describes a system and methods for targeted delivery of an agent for treatment of a respiratory condition. US 2015/290418 A1 is silent on the enhancement of nitric oxide by a better use of the nitric oxide produced by the body itself without a need of external nitric oxide sources.

US 2011/071444 A1 describes devices for the selective excitation of the pharyngeal conduit or another muscle or cartilage along the respiratory path to prematurely reverse the respiratory cycle before the total collapse of the pharyngeal conduit to enable the inhalation stage to reopen and refill the pharyngeal conduit. US 2011/071444 A1 is silent on enhancement of nitric oxide.

WO 2010/071919A1 describes a respiratory aid device that stimulates the chest wall of a user during respiration to reduce breathlessness. WO 2010/071919A1 is silent on enhancement of nitric oxide.

WO 2011/007346 A1 describes a device for the introduction of a fluid into a human's airway. WO 2011/007346 A1 describes that a series of predetermined fluid pressure pulses are accompanied by predetermined humming oscillations for stimulation of NO (nitric-oxide) production.

SUMMARY OF THE INVENTION

The invention is defined by the claims.

Examples in accordance with an aspect of the invention provide a device for controlling the enrichment of nitric oxide levels within the lungs of a subject, comprising:

a detector for detecting the timing of the respiration cycle of the subject, wherein said respiration cycle comprises an alternating occurrence of an inspiration event (or inspiration phase) and an expiration event (or expiration phase);

a stimulator for applying an acoustic or vibratory stimulus to the subject; and a controller adapted to control the stimulator in dependence on the detected timing of the respiration cycle.

Additionally or alternatively, the controller is adapted to control the stimulator in dependence on the detected timing of an event (or a phase) of the respiration cycle.

In normal breathing, and in particular in oral breathing, the nitric oxide (NO) produced in the paranasal sinuses does not reach sufficiently the alveoli. A huge part of the nitric oxide is washed out during expiration (or exhalation). By controlling a stimulator based on the inspiration event (or inspiration phase) of the respiration cycle, a respiration-gated acoustic stimulation is enabled, which can ensure that more nitric oxide from the paranasal sinuses is inspired deep in the lungs. The device stimulates the nitric oxide flow form the sinus only during inspiration (or inhalation) phase and may even block the flow during expiration (or exhalation).

This increase in nitric oxide in the lungs is however made possible without requiring that the device is associated with any external source of nitric oxide.

In one example, the controller is adapted to actuate the stimulator at the beginning of the inspiration (or inhalation) event (or inspiration (or inhalation) phase) of the respiration cycle. The device thus stimulates the outflow of nitric oxide from the sinuses at the onset of an inspiration of the respiration cycle. By providing a dedicated acoustic or vibratory stimulation at the onset of an inspiration of the respiration cycle the nitric oxide flow can be controlled in a way to ensure that the paranasal nitric oxide is nearly fully inspired. This provides a higher nitric oxide concentration in the lung/alveoli. The controller may be adapted to interpret an output signal from the detector to determine the respiration rate, duty cycle and timing of the respiration cycle. By determining these different characteristics of the respiration cycle, the stimulator may be controlled in the most effective manner.

The controller may be adapted to interpret the detector signal to provide a prediction of the timing of the beginning of the next inspiration of the respiration cycle. In this case, the controller may then be adapted to actuate the stimulator a predetermined period of time before the beginning of the inspiration event (or inspiration phase).

In one example, the detector comprises a flow detector for detecting a respiration flow. This may for example be integrated into a patient mask.

In another example, the detector comprises a sensor for sensing chest movement. This provides a way to monitor the respiration without interfering with the breathing of the subject.

In one example, the stimulator comprises a loudspeaker. However, other stimulators may be used, for example a vibrating unit, such as a patch which generates vibrations within the subject without being transmitted to the subject as sound waves through air. The vibrating unit may comprise one or more vibrating elements and/or ultrasonic elements in contact with the subject, preferably the skin of the subject. Such vibrating elements and/or ultrasonic elements configured to generate a vibration transmittable to the subject, preferably the sinus(es) of the subject, for instance via the skin of the user. The stimulator is generally applied to the face of the patient.

The device may comprise a nasal or full face mask and a pressure source for delivering gas to the mask under pressure, wherein the stimulator comprises a pressure controller for controlling the pressure source. In this way, the device is combined with a positive pressure treatment system.

The frequency of the stimulator may be in the range 50 to 1000 Hz. However, the controller is adapted to control the stimulator to operate at a frequency which corresponds to the resonant frequency of a portion of the airway of the subject, for example the paranasal sinus.

Examples in accordance with a second aspect of the invention provide a method of controlling an acoustic or vibratory stimulator, comprising:

detecting the timing of the respiration cycle of a subject, wherein said respiration cycle comprises an alternating occurrence of an inspiration event (or inspiration phase) and an expiration event (or inspiration phase);

applying a vibratory or acoustic stimulus to the subject; and controlling the stimulus in dependence on the detected timing of the respiration cycle. Additionally or alternatively, controlling the stimulus in dependence on the detected timing of an event (or inspiration phase) of the respiration cycle.

The stimulus may be provided at the beginning of an inspiration event (or inspiration phase) of the respiration cycle or a predetermined period of time before the predicted beginning of an inspiration event of the respiration cycle.

The detected timing may be analyzed to determine the respiration rate, duty cycle and timing of the respiration cycle. The stimulus may be at a frequency which corresponds to the resonant frequency of a portion of an airway of a subject.

The method may be computer-implemented such that it is implemented at least in a computer program comprising computer program code means which is adapted, when said computer program is run on a computer, to implement the method as described herein.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a device for controlling the enrichment of the nitric oxide levels within the lungs of a subject. The device comprises a detector for detecting the respiration cycle of the subject and a stimulator for applying an acoustic or vibratory stimulus to the subject. The stimulator is controlled in dependence on the detected respiration cycle. In particular, stimulation may be provided at the onset of inspiration (or inhalation). In this way, the nitric oxide flow can be controlled in a way to ensure that the paranasal nitric oxide is nearly fully inspired. This provides a higher nitric oxide concentration in the lung/alveoli.

Figure 1:
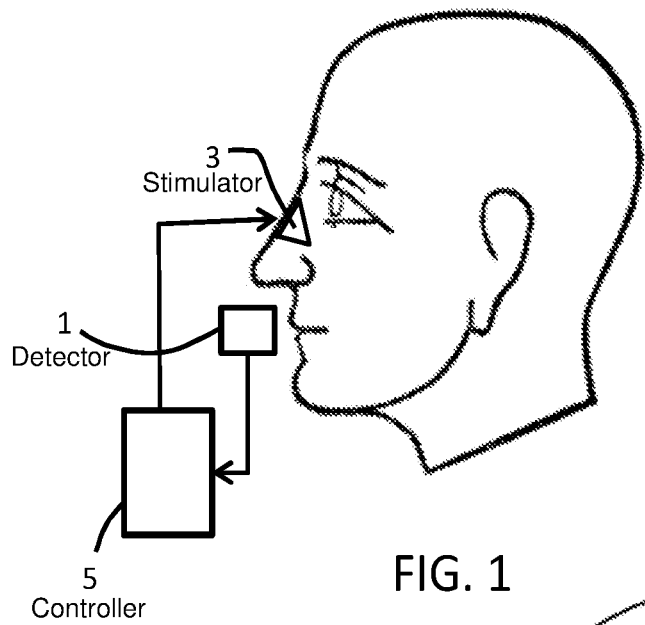
FIG. 1 shows a device for controlling the nitric oxide levels within the lungs of a subject in schematic form.

FIG. 1 shows an example of the device. A detector 1 detects the respiration cycle of the subject. A stimulator 3 applies an acoustic or vibratory stimulus to the subject under the control of a controller 5. The stimulator 3 is controlled in dependence on the detected respiration cycle.

There are various ways to implement the stimulator 3.

A first example is a loudspeaker in the vicinity of the airway or integrated into a nasal mask (or nasal and oral) mask. The frequency is for example in the range of 50-1000 Hz.

Instead of generating an external sound, a source of vibration may be provided which then generates an acoustic vibration within the subject.

For example, a vibrating patch may be attached to the facial skin close to the paranasal sinuses. This is the example represented schematically in FIG. 1.

The controller 5 implements an acoustic signal generator, with the desired frequency range of for example 50-1000 Hz.

The detector is used to determine the timing of different points in the breathing cycle. Most importantly, the detector 1 detects the onset of inspiration, and it may also detect the onset of expiration (or exhalation). The controller then implements the function of a breathing analyzer, to calculate the respiration rate and the inspiration/expiration duty cycle.

The timing of operation of the stimulator is then controlled in dependence on the output from the detector 1.

There are various ways to determine the point within respiration cycle, in particular the onset of inspiration and the onset of expiration (or exhalation). One approach is to measure the air flow (direction and rate) from a subject. This for example may require a mask over the mouth and/or nose and thus interferes with normal respiration. It may be implemented using a nasal thermocouple or flowmeter.

An alternative is to measure the chest movement, for example using an accelerometer applied to the chest.

Another alternative is to monitor a physiological parameter, such as the transthoracic inductance using an impedance plethysmograph, or to take strain gauge measurements of the thoracic circumference. Thermistor measurements may also be used. There are also pneumatic respiration transducers for monitoring the expansion and contraction of the chest. Direct measurements of flow are the most accurate, but interfere with normal respiration, so that indirect measurements are also of interest in many applications.

Based on the monitored breathing rate and cycle of the last few minutes a processing unit is also able to predict the onset of the next breath cycle in advance.

In a simplest implementation, at the start of the inspiration event, the stimulator is controlled for a fixed time, which is shorter than the expected duration of the inspiration event. All that is then needed as a trigger from the detector is the point in time at which the inspiration event begins.

In a more advanced implementation, the stimulator is activated a period of time, such as a few hundred milliseconds (for example in the range 100 ms to 500 ms, e.g. 200 ms) before the start of the predicted next inspiration event.

In a more complete implementation, the respiration duty cycle and timing and the respiration rate are obtained. The frequency, timing, and power of the stimulator are then controlled in dependence on the respiration information. For example, the acoustic stimulation may be provided during the entire inspiration event. The acoustic signal amplitude may be constant but it may also vary as a function of the time within the inspiration event.

In a simplest set of implementations, the stimulator is operated in a simple ON/OFF mode. During the ON mode, the signal strength will be constant. In a more enhanced implementation, the signal strength in the ON mode will linearly decreased from a predefined maximum signal strength to a predefined minimal signal strength.

The stimulation is preferably adapted according to the respiration pattern of the user. That is, the duration of the stimulation during the inspiration phase will take into account the dead space of the upper airway.

During tidal breathing, the inspired volume of air is typically between 400 and 500 ml in male adults. The spatial volume of the upper airway (nasal airway, pharyngeal airway, larynx and main bronchi) is about 150 ml. This is the so-called dead space.

As an approximation, in a tidal volume of for example 450 ml, only 300 ml of the inspired air reaches the alveoli and the tiny bronchiole, 150 ml out of the 450 ml remains in the upper airway and will be blown out during expiration. Any nitric oxide enrichment of the last 150 ml in the airflow in the inspiration phase of the respiration cycle is not effective because it gets lost in the next expiration. Therefore, for this particular example, the stimulation may last only for the first two thirds of the inspiration phase for a typical tidal volume breathing.

In a further implementation, a monitoring device may be used to measure the typically inspired air volume of the patient and calculate the ratio of inspired air and dead space (for instance 750 ml/150 ml). Based on this ratio, the duration of the stimulation may then be determined. In this example, the stimulation will last for 80% of the inspiration phase.

There may be a setting for which the duration deliberately is shorter, for instance when a minor enrichment of nitric oxide is needed.

The device does not make use of any external source of nitric oxide. Instead, it makes use of the natural processes within the body to control the nitric oxide generation and flow.

The frequency of the acoustic stimulation may be selected in dependence on a resonance frequency of the nasal cavity.

The upper airway, the nasal cavity and the sinuses are open cavities. The shape and the volume of each cavities is person-dependent hence the resonance frequency is person-dependent and has to be determined to provide an optimized stimulation therapy.

The acoustic resonance of the sinuses can be analyzed in the same way as analysis of a musical instrument. For a pipe of an organ or the tube of a wind instrument, the acoustic resonance frequency and the frequency harmonics can be determined either empirically by forcing airflow through the tube or theoretically by analyzing the shape of the cavity.

In human beings, the acoustic resonance frequency can be determined either by 3D imaging or by forcing a frequency modulated airflow through the nasal airway. There are for example systems to extract the volumetric shape from tomography images. The algorithms to calculate the resonance are known and described in literature, for example as disclosed in "Acoustic rhinometry in human: accuracy of nasal passage area estimates, and ability to quantify paranasal sinus volume and ostium size", E. Tarhan et. al., J. Appl. Physiol. 99:616-623, 2005.

Alternatively, the resonance frequency can be determined experimentally by measuring the nitric oxide outflow at different stimulation frequencies as disclosed in "Assessment of nasal and sinus nitric oxide output using single-breath humming exhalations", M. Maniscalco et. al., Eur. Respir. J. 2003: 22 323-329.

Thus, the optimal acoustic resonance frequency and the optimal power of the signal may be selected in dependence on the size of the cavity of the paranasal sinus. For each person the resonance frequency can be measured and applied by personalized settings in the stimulator.

Figure 2:
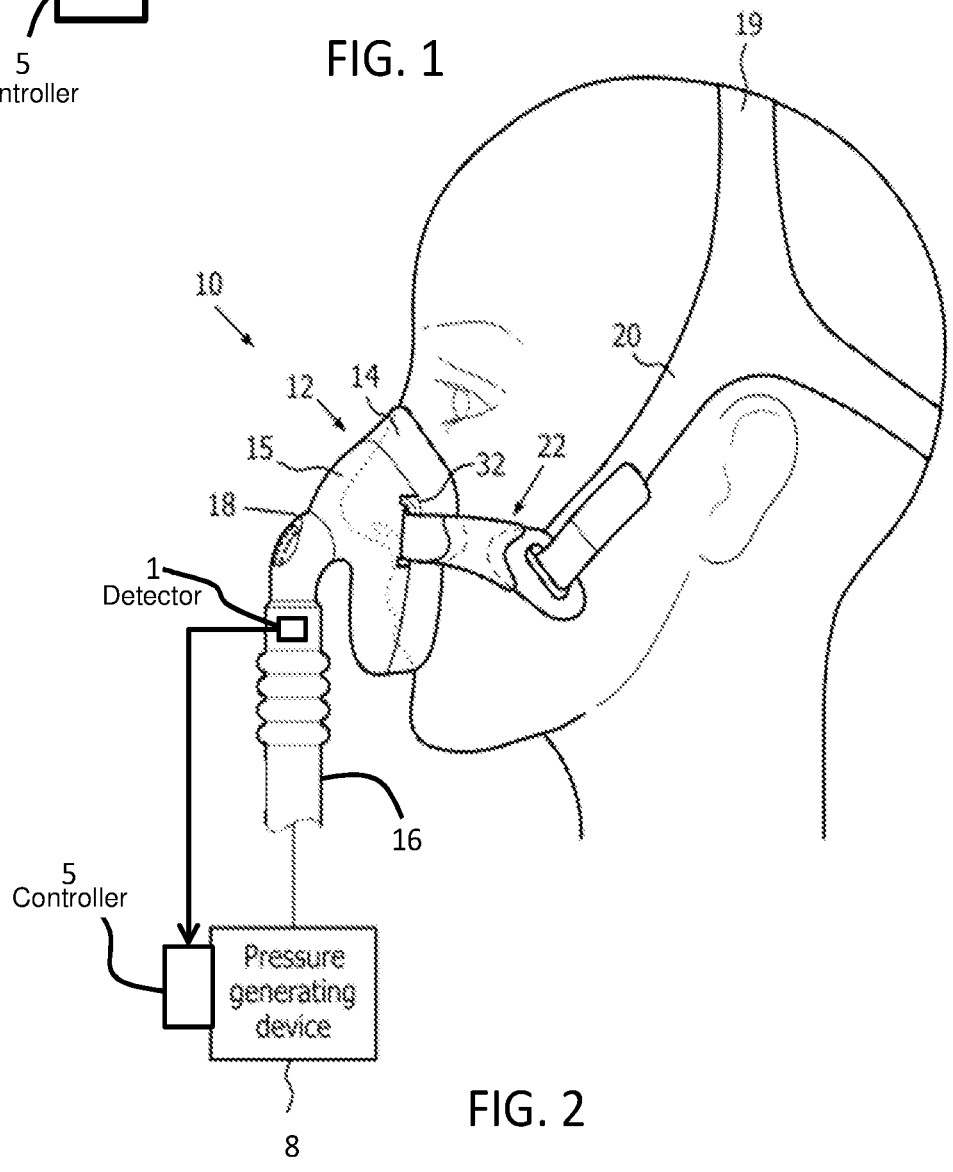
FIG. 2 shows a more detail example of a device for controlling the nitric oxide levels within the lungs of a subject, combined with a positive pressure system.

One implementation of the device is shown in more detail in FIG. 2, in which the device is incorporated into a continuous positive airway pressure (CPAP) system. This system is used to deliver a flow of breathing gas non-invasively to the airway of a patient, i.e. without inserting a tube into the airway of the patient or surgically inserting a tracheal tube in their esophagus. The positive airway pressure is controlled to vary with the patient's respiratory cycle, to treat a medical disorder, such as sleep apnoea syndrome, in particular, obstructive sleep apnea (OSA).

A most basic CPAP system delivers a steady, continuous stream of pressurized air to patient's airways to prevent them from collapsing and causing apnea events. Such CPAP machines are generally set to a single pressure that remains consistent throughout the night. However, many CPAP machines have a ramp feature that starts off with a lower pressure setting and gradually builds to the prescribed pressure. Furthermore, a respiration/flow sensor may also be used to detect the respiration cycle and determine the respiration rate and the inspiration duty cycle.

A bi-level positive airway pressure (BiPAP) system includes a breath timing feature that measures the amount of breaths per minute and can set a limit. If the time between breaths exceeds the set limit, the machine can force the person to breathe by temporarily increasing the air pressure. BiPAP machines thus have two pressure settings: the prescribed pressure for inhalation (IPAP), and a lower pressure for exhalation (EPAP). The dual settings allow the patient to get more air in and out of their lungs.

Such non-invasive ventilation and pressure support therapies involve the placement of a patient interface device including a mask component on the face of a patient. The mask component may be, without limitation, a nasal mask that covers the patient's nose, a nasal pillow/cushion having nasal prongs that are received within the patient's nostrils, a nasal/oral mask that covers the nose and mouth, or a full face mask that covers the patient's face. The patient interface device interfaces between the ventilator or pressure support device and the airway of the patient, so that a flow of breathing gas can be delivered from the pressure/flow generating device to the airway of the patient.

FIG. 2 shows a system to provide respiratory therapy to a patient. This is termed a "patient interface assembly". It is modified to additionally provide the acoustic stimulation described above.

The assembly includes a pressure generating device 8 and a patient interface 10.

The patient interface 10 includes a mask 12, which in the exemplary embodiment is a nasal and oral mask covering the nose and mouth. However, any type of mask, such as a nasal-only mask, a nasal pillow/cushion or a full face mask, which facilitates the delivery of the flow of breathing gas to the airway of a patient, may be used as mask 12. The mask 12 includes a cushion 14 coupled to a shell 15. The cushion 14 is made of a soft, flexible material, such as, without limitation, silicone, an appropriately soft thermoplastic elastomer, a closed cell foam, or any combination of such materials. An opening in shell 15 allows the flow of breathing gas from pressure generating device 8 to be communicated to an interior space defined by the shell 15 and cushion 14, and then to the airway of a patient.

From the pressure generating device, a delivery conduit 16 is coupled to an elbow connector 18 of the patient interface 10. The pressure generating device 8 is structured to generate a flow of breathing gas and may include, without limitation, ventilators, constant pressure support devices (such as a continuous positive airway pressure device, or CPAP device), variable pressure devices, and auto-titration pressure support devices.

Delivery conduit 16 communicates the flow of breathing gas from pressure generating device 8 to patient interface 10 through the elbow connector 18. The delivery conduit 16, elbow connector 18 and patient interface 10 are often collectively referred to as a patient circuit.

The detector 1 is in the form of a flow sensor provided in the conduit 16 for monitoring the flow of gas to or from the patient, in order to determine in a direct way the time within the respiration cycle. The controller 5 controls the pressure generating device to create an acoustic signal, by modulating a suitable high frequency signal on the pressure delivered by the pressure generating device 8.

The assembly also includes a headgear component 19, which in the illustrated embodiment is a two-point headgear. Headgear component 19 includes a first and a second strap 20, each of which is structured to be positioned on the side of the face of the patient above the patient's ear. Headgear component 18 further includes a first and a second mask attachment element 22 to couple the end of one of the straps 20 to the respective side of the mask 12.

It is also known to include a forehead support to spread the required forces over a larger area. In this way, an additional cushion support on the forehead balances the forces put by the mask around the nose or nose and mouth. This can be used to address a problem that the headgear force vectors necessary to achieve a robust and stable seal against the face of the patient can cut a straight line near the corners of a patient's eyes, which can be uncomfortable and distracting.

The CPAP or BiPAP systems already provide much of the hardware required to implement the acoustic stimulation device described above.

For example, at least some CPAP systems, and all BiPAP systems, already include monitoring of the respiration cycles of the user, and the same monitoring may be used to control the acoustic stimulation.

The acoustic vibrations themselves may be provided by a modulation of the airway pressure provided by the pressure generating device 8. Thus, the acoustic stimulation system may be implemented by extending the functionality of the controller of the CPAP or BiPAP system to activate and control the stimulator.

The pressure of a CPAP and BiPAP device is typically in the range of 4 to 20 cm $H_2O$ (approximately 400 Pa to 2000 Pa). A PAP device detects the spontaneous breathing of the person and adapts the pressure to the monitored person's breathing pattern. Hence the low frequency pressure modulation in a BiPAP device is synchronized with the respiration frequency.

The paranasal sinus is the largest of the nasal sinuses. Due to its larger cavity it is the greatest reservoir of nitric oxide. The typical resonance frequency of the paranasal sinus is about 200 Hz. A stimulation frequency of 200 Hz may thus be the default frequency setting of the device. The smaller nasal sinuses have a higher resonance frequency of up to 1000 Hz.

In an advanced implementation the stimulator may stimulate at multiple discrete frequencies, e.g. 200 Hz, 500 Hz, 1000 Hz.

The combination of the acoustic stimulation system with a CPAP or BiPAP system is not essential. For example, the stimulator and the controller may be integrated into a nasal mask or a nasal/oral mask, without the need to apply continuous or bi-level pressure. The device may then only be for controlling the nitric oxide levels.

As mentioned above, the stimulator may instead be integrated into a patch that is attached to the facial skin close the paranasal sinus.

The invention is of interest for the treatment of pulmonary hypertension, for relaxation of constricted bronchi, and for vasodilatation of pulmonary blood vessels.

As discussed above, the controller 5 implements the control method. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform at the required functions. Various storage media may be fixed within a processor or controller or may be transportable, such that the one or more programs stored thereon can be loaded into a processor or controller.

Additionally or alternatively, a device for controlling enrichment of nitric oxide levels within the lungs of a subject, comprising, a detector (1) for detecting a timing of a respiration cycle of the subject, a stimulator (3) for applying an acoustic or vibratory stimulus to the subject and a controller (5) adapted to control the stimulator in dependence on the detected timing of the respiration cycle.

Additionally or alternatively, a method of controlling an acoustic or vibratory stimulator, comprising, detecting the timing of the respiration cycle of a subject, applying a vibratory or acoustic stimulus to the subject and controlling the stimulus in dependence on the detected timing of the respiration cycle.

In the claims, any reference signs placed between parentheses shall not be construed as limiting the claim. The word "comprising" or "including" does not exclude the presence of elements or steps other than those listed in a claim. The word "a" or "an" preceding an element does not exclude the presence of a plurality of such elements. The mere fact that certain elements are recited in mutually different dependent claims does not indicate that these elements cannot be used in combination. Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the scope of the appended claims. For example, it is to be understood that the present invention contemplates that, to the extent possible, one or more features of any embodiment can be combined with one or more features of any other embodiment.

The invention claimed is:

1. A device for controlling enrichment of nitric oxide levels within lungs of a subject, the device comprising:
   a detector for detecting a timing of a respiration cycle of the subject, wherein said respiration cycle comprises an alternating occurrence of an inspiration event and an expiration event;
   a stimulator for applying an acoustic or vibratory stimulus to a sinus of the subject; and
   a controller in communication with the detector and adapted to control the stimulator in dependence on the detected timing of the respiration cycle and/or an event of the respiration cycle,
   wherein the controller is further adapted to interpret an output signal of the detector to provide a prediction of the timing of the beginning of a next inspiration event of the respiration cycle, and
   wherein the controller is adapted to actuate the stimulator only for a length of time beginning a predetermined period of time before the beginning of each inspiration event of the respiration cycle and ending at or before the end of each inspiration event of the respiration cycle.

2. A device as claimed in claim 1, wherein the detector is adapted to provide an output signal and the controller is adapted to interpret the output signal of the detector to determine the respiration rate, duty cycle and timing of the respiration cycle.

3. A device as claimed in claim 1, wherein the detector comprises a flow detector for detecting a respiration flow or a sensor for sensing chest movement.

4. A device as claimed in claim 1, comprising a nasal or full face mask and a pressure source for delivering pressurized gas to the nasal or full face mask, wherein the controller comprises a pressure controller for controlling the pressure source.

5. A device as claimed in claim 1, wherein the frequency of the stimulator is in the range 50 to 1000 Hz.

6. A device as claimed in claim 1, wherein the device is not associated with any external source of nitric oxide.

7. A device as claimed in claim 1, wherein the controller is adapted to control the stimulator to operate at a frequency which corresponds to a resonant frequency of a paranasal sinus.

8. A device as claimed in claim 1, wherein the stimulator comprises a loudspeaker.

9. A device as claimed in claim 1, wherein the controller is adapted to control the stimulator such that the stimulus is provided only during a portion of each inspiration phase.

10. A device as claimed in claim 1, wherein the controller is adapted to control the stimulator such that the stimulus is provided with an amplitude that varies as a function of time.

11. A device as claimed in claim 1, wherein the controller is adapted to control the stimulator such that the stimulus is provided with a decreasing acoustic strength over time.

12. A device as claimed in claim 1, wherein the stimulator is for applying the stimulus to a paranasal sinus of the subject.

13. A method of controlling an acoustic or vibratory stimulator, comprising:
- detecting a timing of the respiration cycle of a subject, wherein said respiration cycle comprises an alternating occurrence of an inspiration event and an expiration event;
- applying a vibratory or acoustic stimulus to a sinus of the subject,
- controlling the stimulus in dependence on the detected timing of the respiration cycle and/or an event of the respiration cycle; and
- providing the stimulus only for a length of time beginning at a predetermined period of time before a predicted beginning of each inspiration event of the respiration cycle and ending at or before the end of each inspiration event of the respiration cycle.

14. A method as claimed in claim 13, comprising interpreting the detected timing to determine the respiration rate, duty cycle and timing of the respiration cycle.

15. A method as claimed in claim 13, wherein the vibratory or acoustic stimulus has a frequency which corresponds to a resonant frequency of a paranasal sinus.

16. The method of claim 13, wherein controlling the stimulus comprises applying the stimulus only during a portion of each inspiration event.

17. The method of claim 13, wherein controlling the stimulus comprises applying the stimulus with an amplitude that varies as a function of time.

18. The method of claim 13, wherein controlling the stimulus comprises applying the stimulus at an acoustic strength that decreases over time.

19. The method of claim 13, wherein applying the stimulus to sinus of the subject comprises applying the stimulus to paranasal sinus of the subject.

* * * * *